US00PP31214P2

(12) United States Plant Patent
Hansen

(10) Patent No.: US PP31,214 P2
(45) Date of Patent: Dec. 10, 2019

(54) ***PHLOX* PLANT NAMED 'ROSE SPRITE'**

(50) Latin Name: ***Phlox* hybrid**
Varietal Denomination: Rose Sprite

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,549

(22) Filed: Nov. 30, 2018

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique cultivar of hybrid creeping *Phlox* named *Phlox* 'Rose Sprite' multi-stemmed, short, upright, slowly-spreading habit with clean, green, glossy, lanceolate to linear leaves with exceptional powdery mildew resistance. Flowers held above foliage on wine-colored stems with petals of rose-pink with white center halo and dark purple markings at center, nearly covering the top of the plant in peak flowering season about one week later than typical *Phlox subulata*. 'Rose Sprite' is especially useful as a container-ized plant and for the flower garden as an specimen or en masse.

1 Drawing Sheet

Botanical classification: *Phlox* hybrid.
Variety denomination: 'Rose Sprite'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Dec. 1, 2017 the claimed plant was displayed with photographs and brief description on a website of Walters Gardens, Inc., who obtained the plant and all information relating thereto, from the inventor. No plants of *Phlox* 'Rose Sprite' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Rose Sprite' and will be referred to hereafter by its cultivar name or the "new plant". The new plant was the result of a cross of *Phlox subulata* 'Apple Blossom' (not patented) as the female or seed parent and an unnamed selection of *Phlox procumbens* as the male or pollen parent is unknown performed at a wholesale perennial nursery in Zeeland, Mich. on Mar. 31, 2014. The new plant was given the breeder code 14-308-5 prior to naming and throughout subsequent evaluations at the same nursery. 'Rose Sprite' has been asexually propagated by stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Rose Sprite' is unique from its parents and all other hybrid creeping *Phlox* or other *Phlox* known to the inventor. The new plant differs from the female parent, 'Apple Blossom', in that the female parent has more narrow, near-white petals with reddish marks near the center, the habit is shorter, and the growth rate faster and less manageable in the landscape. The male parent is taller and looser in habit and the foliage is larger, broader and more pubescent. The closest comparison cultivars known to the inventor are the copending application Ser. No. 16/350,550 *Phlox* 'Magenta Sprite', 'PPPHL0604' U.S. Plant Pat. No. 23,703 ('Britney'), 'PPPHL07101' U.S. Plant Pat. No. 24,007 ('Lindsay'), 'PPPHL07201' U.S. Plant Pat. No. 26,854, PPPHL07301' U.S. Plant Pat. No. 23,702 ('Angelina'), PPPHL07201' U.S. Plant Pat. No. 23,705 ('Paris') and 'PHL090401' U.S. Plant Pat. No. 26,852 ('Levine'). 'Magenta Sprite' has a smaller white halo in the center of the flower and the petal color is more magenta pink. 'PPHL0604' is taller in habit, has flower color that begin a bright pink with white center eye and lacks dark purple markings near center. 'PPPHL07101' is slightly taller in habit, the petals begin a strong purplish red and lack the center purple markings. 'PPPHL07301' is taller in habit and has flowers that have a near-white eye zone and petals of a medium purple. 'PHL090201' has a slightly taller habit, the flower petals are narrower and dark lavender colored. 'PPPHL070201' has slightly taller habit and the flowers are violet-blue with a dark eye. 'PHL090401' has slightly taller habit and the flowers are lavender with narrower petals.

'Rose Sprite' differs from all other *Phlox* known to the inventor in the following repeatedly observed traits in combination:

1. Plants of short mounded habit, slowly spreading by short rhizomes, producing clean, glossy, clean green, lanceolate to linear leaves;

2. Showing exceptional powdery mildew resistance;
3. Multiple branched, wine-colored stems produce rounded mounds of flowers starting in mid-spring;
4. Faintly-sweet fragrant flowers on mounded stems of about 14.0 cm tall;
5. Flowers are rose-pink with dark purple markings in the center and developing a white eye zone;
6. Flowers densely cover nearly the entire top of the plant;
7. Flowering about one week after typical *Phlox subulata* cultivars.

BRIEF DESCRIPTION OF THE DRAWINGS

The photographs of the new plant demonstrate the unique traits of 'Rose Sprite' and the overall appearance of the plant at two-years-old grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
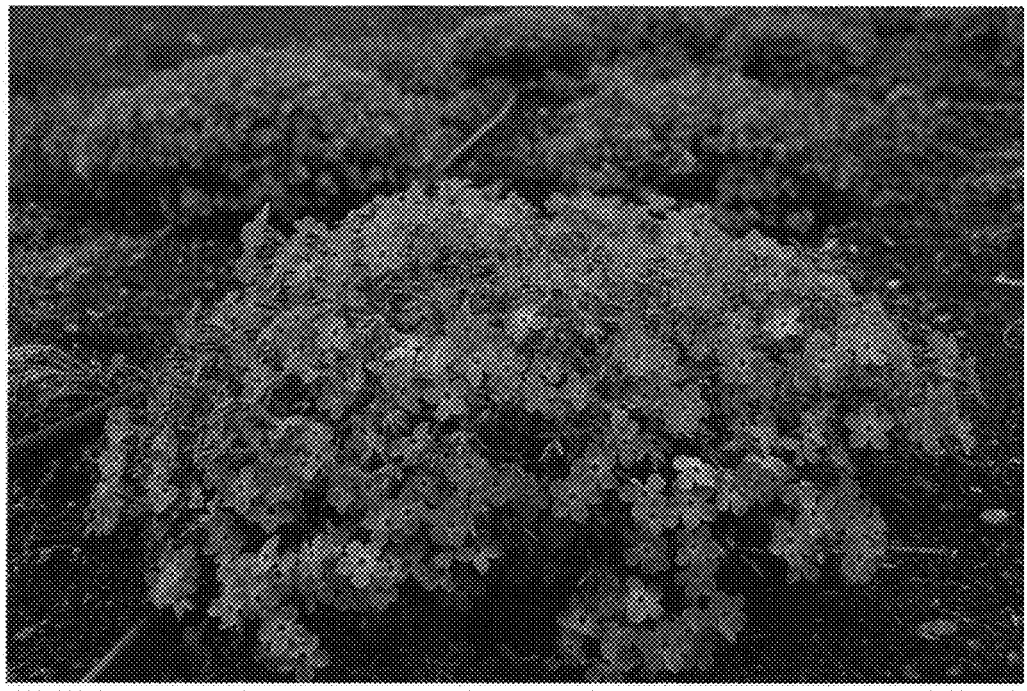
FIG. 1 shows the habit of the new plant in peak flower.
Figure 2:
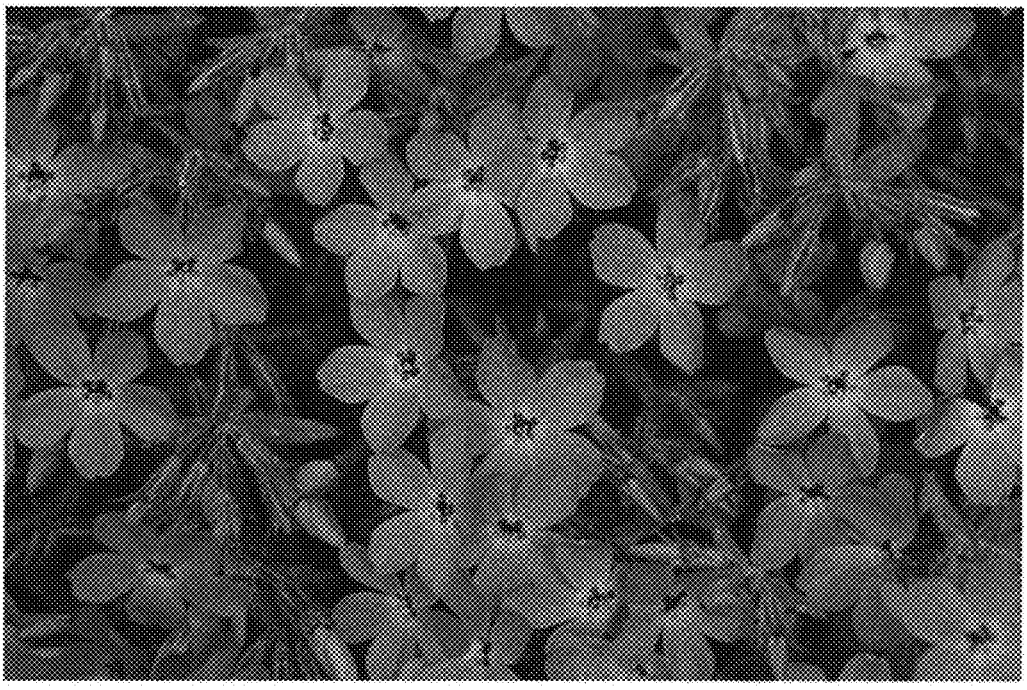
FIG. 2 shows a close-up of the flowers of different ages and buds.

The following descriptions and color references are based on the 2015 edition of The Royal Horticultural Society Colour Chart except where common dictionary terms are used. *Phlox* 'Rose Sprite' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full-sun trial garden of a wholesale perennial nursery in Zeeland, Mich. with supplemental fertilizer and water as needed.

Botanical classification: *Phlox* hybrid;

Parentage: Female or seed parent *Phlox subulata* 'Apple Blossom' and the male or pollen parent an unnamed selection of *Phlox procumbens;*

Plant habit: Densely-mounded, winter-hardy, herbaceous perennial, producing branched stems and early spring flowering; with foliage to about 8.0 cm tall and about 38.0 cm wide; densely flowering about one week after typical *Phlox subulata* cultivars and continuing for about 4 weeks;

Propagation: Stem cuttings; rooting in about 14 days;

Time to produce finished crop in 3.8 liter pots: About 12 to 14 weeks; moderate rate of growth;

Root: Primary roots to about 1.0 mm thick; secondary fibrous and freely branching; color creamy white to tan depending on soil type and root stage of development;

Leaves: Simple; opposite; lanceolate to linear; entire margin; narrowly acute apex; truncate base; sessile; slightly folded;

Leaf size: To about 29.0 mm long by about 6.0 mm wide, average about 18.0 mm long by about 5.0 mm wide;

Leaf surfaces: Matte and sparsely puberulent adaxial and matte and puberulent abaxial;

Leaf color expanding: Adaxial nearest RHS 137B distally and RHS 145A proximally, and abaxial nearest RHS 146B distally and nearest RHS 146D proximally;

Leaf color at flowering: Adaxial and abaxial base nearest RHS 145B and adaxial proximally nearest RHS 137A and abaxial proximally nearest RHS 146B;

Foliage fragrance: None detected;

Veins: Pinnate; glabrous adaxial and abaxial; midrib about 0.5 mm wide at base, slightly sunken adaxial and raised abaxial; color proximal adaxial midrib nearest RHS 146C, abaxial midrib same as surrounding leaf tissue, other veins not noticeable;

Petiole: Leaves sessile;

Stems: Cylindrical; flexible; strong; pubescent; proximally rosulate and distally decussate; average about 9.0 cm long and 2.0 mm diameter at base;

Stem color: Lower portion covered with leaves, distally nearest RHS N186C in areas receiving high light exposure;

Nodes: About five per stem in branched peduncle region and 30 to 40 in lower portion; average internode length about 0.5 cm;

Node color: Nearest RHS N186C;

Inflorescence: A loosely-branched compound corymb of about 22 flowers; about 8.0 cm long and 6.0 cm across;

Flowers: Perfect; salverform with flat face and long fused corolla tube; actinomophic; typically with five petals; attitude upright to outwardly;

Flower size: About 22.0 mm across face and 21.0 mm long to exserted stigma; corolla tube about 15.0 mm long and about 2.5 mm diameter below face;

Flower longevity: About 5 days; self-cleaning;

Flower fragrance: Lightly sweet;

Buds one to two days prior to opening: Narrowly oblanceolate, to nearly clavate; acute apex with convolute petals; base fused; about 18.0 mm long and 2.5 mm diameter in tube base and swollen to 4.0 mm diameter toward apex of convolute petals;

Bud color: Exposed petals nearest RHS N81D and distal 2.0 mm of exposed tube more grey than RHS 83B or RHS 86B;

Petals: Five; limb obtuse, apex rounded and emarginate notched to 1.0 mm deep; base fused into tube; margin entire; abaxial limb glabrous and tube micro-puberulent, adaxial limb glabrous, adaxial tube glabrous except pubescent in 2.0 mm portion between 2.0 mm and 4.0 mm above base; broad white halo in center 3.0 mm of face with two dark purple marks, about 1.0 mm long and 0.5 mm wide;

Petal size: Basal 15.0 mm fused into corolla tube, to a diameter of about 2.5 mm; limb face about 8.5 mm across, and face about 10.0 mm long; slightly imbricate toward center;

Petal color: Adaxial face center between RHS N74C and RHS NN74C with white center halo nearest RHS NN155D and two dark purple marks of nearest RHS 79B; abaxial limb between RHS 75A and RHS 75B with center halo nearest RHS NN155D; adaxial corolla tube base nearest RHS 145D and distally nearest RHS 79C; abaxial base nearest RHS 145D and distally nearest RHS N82D and proximally and above base more grey than RHS 79C;

Androecium:

*Filaments.*—Typically five; adnate to adaxial inner corolla at various distances of 7.0 mm to 13.0 mm from base; free in terminal 0.5 mm; color nearest RHS 76C.

*Anther.*—Five; oblong elliptic; basifixed; longitudinal; about 1.2 mm long by 0.5 mm wide; color between RHS 23C and RHS 23B.

*Pollen.*—Abundant; color nearest RHS 23A.

Gynoecium: One pistil per flower; to about 20.0 mm long; superior;

*Style.*—Cylindrical; about 19.0 mm long and about 0.2 mm diameter; color nearest RHS 145D in basal one-third and transitioning to nearest RHS NN155A in distal one-half.

*Stigma.*—Trifurcate in the distal 1.5 mm, less than 0.2 mm in diameter; persistent after flower abscission; color nearest RHS 8C.

*Ovary.*—Superior; globose with acute apex and truncate base; about 1.5 mm long and 1.0 mm diameter; color nearest RHS 143A.

Calyx: Tubular to campanulate; adpressed to corolla tube in proximal half and reflexed distal in distal half; to about 7.5 mm long and 8.0 mm wide at apex;

Sepals: Five; linear; narrowly acute apex, margin entire; basal 3.0 mm fused; surface matte and glandular abaxial, lustrous and glabrous adaxial; individually about 10.0 mm long and 1.0 mm wide;

Sepal color: Abaxial nearest RHS 137D; adaxial nearest RHS 137B with light blushing of nearest RHS 83D in strong light exposure; margins nearest RHS 158D;

Peduncle: Pubescent; flexible, strong, mostly upright; cylindrical; flowering portion about 6.0 cm long and 2.0 mm diameter at base of flower branches; branches to about 5.0 cm long and 2.0 mm diameter at base; typically five flowers per branch;

Peduncle color: Variable; nearest RHS N144D in low light exposure and blushed with nearest RHS 183C in regions of high light exposure;

Pedicel: Terete; pubescent; variable lengths from about 6.0 mm long and 15.0 mm diameter; Pedicel color: Nearest RHS 146C with variable blush of nearest RHS 183C; Fruit and seeds have not yet been observed;

Hardiness and culture: The new plant grows best with plenty of moisture and adequate drainage; prefers full sun but tolerates light shade; is hardy to at least from USDA zone 3 through 8.

Disease and pest resistance: *Phlox* 'Rose Sprite' demonstrated the excellent resistance to powdery mildew caused by *Erysiphe cichoracearum* under conditions of intense pressure that would normally show symptoms.

I claim:

1. A new and distinct cultivar of hybrid *Phlox* plant named *Phlox* 'Rose Sprite', as herein described and illustrated.

* * * * *